(12) United States Patent
Minagawa et al.

(10) Patent No.: US 8,207,301 B2
(45) Date of Patent: Jun. 26, 2012

(54) HEPATOCELLULAR CARCINOMA PROTEIN MARKER

(75) Inventors: Hirotaka Minagawa, Tokyo (JP); Kenji Miyazaki, Tokyo (JP); Yo Tabuse, Tokyo (JP); Kenichi Kamijo, Tokyo (JP); Shuichi Kaneko, Ishikawa (JP)

(73) Assignee: NEC Corporation, Tokyo (JP)

( * ) Notice: Subject to any disclaimer, the term of this patent is extended or adjusted under 35 U.S.C. 154(b) by 197 days.

(21) Appl. No.: 12/452,216

(22) PCT Filed: Jun. 16, 2008

(86) PCT No.: PCT/JP2008/061375
§ 371 (c)(1),
(2), (4) Date: Dec. 22, 2009

(87) PCT Pub. No.: WO2008/156183
PCT Pub. Date: Dec. 24, 2008

(65) Prior Publication Data
US 2010/0248256 A1 Sep. 30, 2010

(30) Foreign Application Priority Data
Jun. 20, 2007 (JP) .................................. 2007-162857

(51) Int. Cl.
*C07K 14/435* (2006.01)

(52) U.S. Cl. ....................................... 530/350; 530/352

(58) Field of Classification Search ........................ None
See application file for complete search history.

(56) References Cited

U.S. PATENT DOCUMENTS
2004/0072255 A1 4/2004 Van Eyk et al.

FOREIGN PATENT DOCUMENTS
JP 3129430 11/2000
JP 2006-502203 1/2006

OTHER PUBLICATIONS

Liebman HA, Furie BC, Tong MJ, Blanchard RA, Lo KJ, Lee SD, Coleman MS, and Furie B., New Engl. J. Med. vol. 310, No. 22, pp. 1427-1431. (1984), De-sy-Carboxy (Abnormal) Prothrombin as a Serum Marker of Primary Hepatocellular Carcinoma.
Kumagai Y, Chiba J, Sata T, Ohtaki S, and Mitamura K. Cancer Res. 52, pp. 4987-4994. (1992),"A New Tumor-associated Antigen Useful for Serodiagnosis of Hepatocellular Carcinoma, Defined by Monoclonal Antibody KM-2".
John Elias, et al., Int. J. Cancer. 46, pp. 805-807. (1990), "Evaluation of CA 125 as a Serum Marker of Hepatocellular Carcinoma".
Kenji Tanaka, et al., "Enhanced expression of mRNAs of antisecretory factor-1, gp96, DAD1 and CDC34 in human hepatocellular carcinomas", Biochim. Biophys, Acta, 2001, vol. 1536, p. 1-12.
Yao, D.-F., et al., Abnormal expression of HSP gp96 associated with HBV replication in human hepatocellular carcinoma, Hepatobiliary Pancreat, Dis. Int., 2006, vol. 5., No. 3, p. 381-386.
Moran, M. F., et al., Emerging application for phospho-proteomics in cancer molecular therapeutics, Biochim. Biophys. Acta, 2006, vol. 1766, p. 230-241.
Masao Honda, et al., "Morateki Idenshi Hatsugen Kaiseki to Kan Tando Shikkan", Bessatsu Igaku no Ayumi, 2006, pp. 211 to 215.
Kanji Sugita, et al., "Ko Rinsanka Thyrosin Kotai o Mochiita Ph Yosei Kyusei Lymph-sei Hakketsubyo no Shindan"; Igaku no Ayumi, 1994, vol. 170, No. 11, pp. 966 to 968.
Zhu, X.-D., et al., Significant correlation between expression level of HSP gp96 and progression of hepatitis B virus induced diseases, World J. Gastroenterol., 2004, vol. 10, No. 8, p. 1141-1145.

*Primary Examiner* — Prema Mertz
(74) *Attorney, Agent, or Firm* — McGinn IP Law Group, PLLC

(57) ABSTRACT

Provided are: a method of assessing hepatocellular carcinoma by using a protein with a different phosphorylated state in hepatocellular carcinoma cells compared with non-hepatocellular carcinoma cells; and a hepatocellular carcinoma protein marker for detecting hepatocellular carcinoma formed of the protein. The hepatocellular carcinoma protein marker for detecting hepatocellular carcinoma includes tumor rejection antigen gp96 formed of the amino acid represented by SEQ ID NO: 1, and is measured for its phosphorylated state to detect the presence or absence of hepatocellular carcinoma.

2 Claims, 4 Drawing Sheets

1 MRALWVLGLC CVLLTFGSVR ADDEVDVDGT VEEDLGKSRE GSRTDDEVVQ
51 REEEAIQLDG LNASQIRELR EKSEKFAFQA EVNRMMKLJI NSLYKNKEIF
101 LRELISNASD ALDKIRLISL TDENALSGNE ELTVKIKCDK EKNLLHVTDT
151 GVGMTREELV KNLGTIAKSG TSEFLNKMTE AQEDGQSTSE LIGQFGVGFY
201 SAFLVADKVI VTSKHNNDTQ HIWESDSNEF SVIADPRGNT LGRGTTITLV
251 LKEEASDYLE LDTIKNLVKK YSQFINFPIY VWSSKTETVE EPMEEEAAK
301 EEKEESDDEA AVEEEEEKK PKTKKVEKTV WDWELMNDIK PIWQRPSKEV
351 EEDEYKAFYK SFSKESDDPM AYIHFTAEGE VTFKSILFVP TSAPRGLFDE
401 YGSKKSDYIK LYVRRVFITD DFHDMMPKYL NFVKGVVDSD DLPLNVSRET
451 LQQHKLLKVI RKKLVRKTLD MIKKIADDKY NDTFWKEFGT NIKLGVIEDH
501 SNRTRLAKLL RFQSSHHPTD ITSLDQYVER MKEKQDKIYF MAGSSRKEAE
551 SSPFVERLLK KGYEVIYLTE PVDEYCIQAL PEFDGKRFQN VAKEGVKFDE
601 SEKTKESREA VEKEFEPLLN WMKDKALKDK IEKAVVSQRL TESPCALVAS
651 QYGWSGNMER IMKAQAYQTG KDISTNYYAS QKKTFEINPR HPLIRDMLRR
701 IKEDEDDKTV LDLAVVLFET ATLRSGYLLP DTKAYGDRIE RMLRLSLNID
751 PDAKVEEEPE EEPEETAEDT TEDTEQDEDE EMDVGTDEEE ETAKESTAEK
801 DEL

FIG. 2

(a)
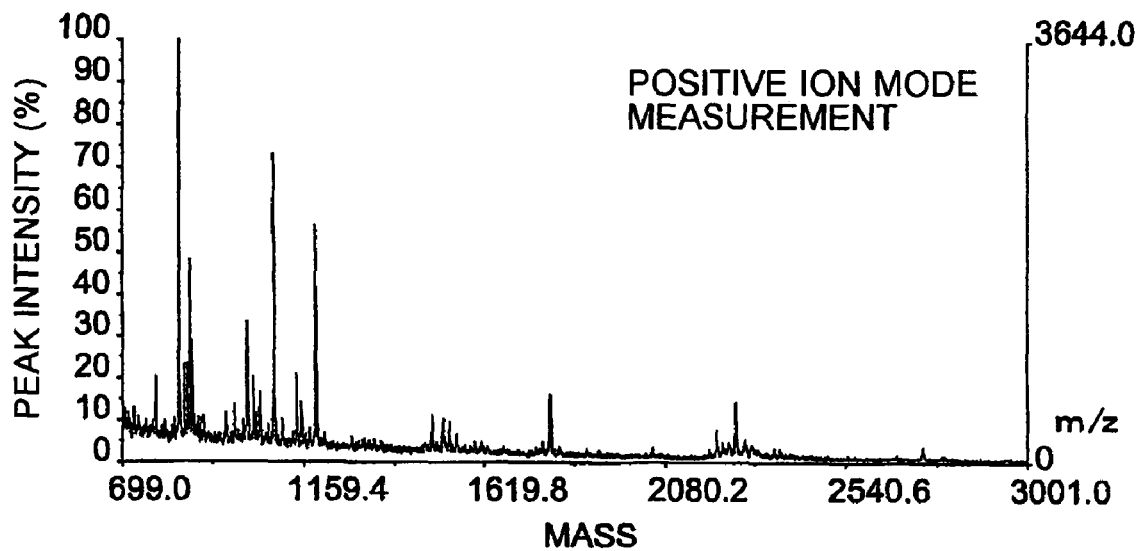
(b)
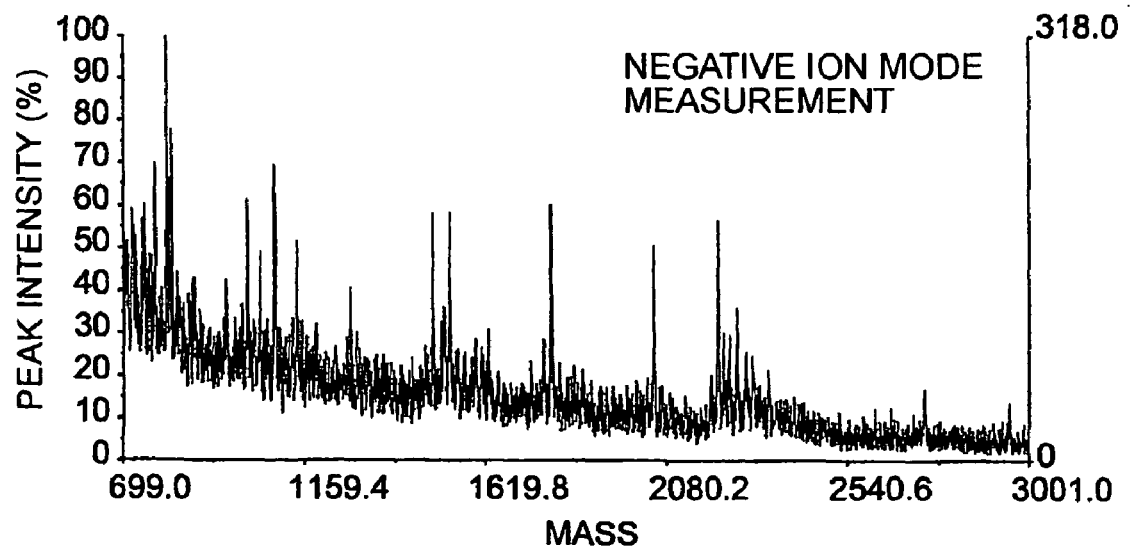
FIG. 3

HEPATOCELLULAR CARCINOMA PROTEIN MARKER

Incorporated by reference herein is the sequence listing including in the text file having a file name "Sequence Listing.txt" which was created on Jun. 11, 2010 and has a size of 7 KB.

TECHNICAL FIELD

This invention relates to a phosphorylating-modified, i.e. phosphorylated, protein marker that can be used in detection of hepatocellular carcinoma and a method of detecting a hepatocellular carcinoma including a step of using the protein marker.

BACKGROUND ART

The hepatocellular carcinoma is one of epithelial malignant tumors developed as a primary carcinoma in a liver and formed of tumor cells similar to hepatocytes. In general, a large number of tumors are formed in a liver and are likely to grow and progress in a hepatic vessel, and a tumor thrombosis is frequently formed in a portal vein. The hepatocellular carcinoma often breaks out in the Asian region including Japan and the African region, and cirrhosis concurs in many cases.

As a marker for detecting hepatocellular carcinoma, use is made have been conventionally of α-fetoprotein (AFP) and PIVKA-II (see Non-patent Document 1), KM-2 (see Non-patent Document 2), CA125 (see Non-patent Document 3), and the like.

Meanwhile, it is known that a post-translational modified, in particular, phosphorylated protein reflects conditions of various organs and tissues. For example, a phosphorylated troponin 1 protein for recognizing a condition of a muscle tissue that has suffered damage (see Patent Document 1); and phosphorylated urokinase to be used for detecting various types of carcinoma (see Patent Document 2).

[Non-patent Document 1] Liebman H A, Furie B C, Tong M J, Blanchard R A, Lo K J, Lee S D, Coleman M S, and Furie B., New Engl. J. Med. 310, pp. 1427-1431. (1984)

[Non-patent Document 2] Kumagai Y, Chiba J, Sata T, Ohtaki S, and Mitamura K. Cancer Res. 52, pp 4987-4994. (1992)

[Non-patent Document 3] Elias J, Kew M C. Int. J. Cancer. 46, pp 805-807. (1990)

[Patent Document 1] JP-A-2006-502203, Title of the Invention "ISOLATED POST-TRANSLATIONALLY MODIFIED PROTEINS FOR MONITORING AND DIAGNOSING MUSCLE DAMAGE"

[Patent Document 2] JP-B-3129430, Title of the Invention "METHOD FOR DETECTING TUMOR DISEASE"

DISCLOSURE OF THE INVENTION

Problem to be Solved by the Invention

However, markers disclosed in Non-patent Documents 1 to 3 have not been sufficient in assessment rate of positive results.

For example, the screening rates of AFP and PIVKA-II in hepatocellular carcinoma assessment are 60% to 70%. Therefore, there is a demand for a marker with additional reliability.

An object of this invention is to provide a protein other than those described in the above-mentioned Patent Documents 1 and 2, including a method of assessing hepatocellular carcinoma by using a protein which is present in a hepatocellular carcinoma cell in a different phosphorylated state from that in a non-hepatic carcinoma cell.

Further, another object of this invention is to provide a hepatocellular carcinoma protein marker for detecting the hepatocellular carcinoma, including a protein having a different phosphorylated state.

Means to Solve the Problem

According to an aspect of this invention, there is provided a hepatocellular carcinoma protein marker, which includes tumor rejection antigen gp96 formed of an amino acid represented by SEQ ID NO: 1, in which the protein marker is phosphorylated.

According to another aspect of this invention, there is provided a method of detecting hepatocellular carcinoma which includes using the hepatocellular carcinoma protein marker as above-described.

According to still another aspect of this invention, there is provided a method of detecting hepatocellular carcinoma as above-described. In the method, the using the protein marker includes extracting from a surgically sampled biological sample.

According to yet another aspect of this invention, there is provided a method of detecting hepatocellular carcinoma as above-described. In the method, the using the protein marker further includes preparing the biological sample which includes any one kind of a biopsy sample, blood, plasma, serum, and urine.

According to a further aspect of this invention, there is provided a method of detecting hepatocellular carcinoma as above-described. In the method, the using the protein marker includes verifying phosphorylation of the protein marker.

According to a still further aspect of this invention, there is provided a method of detecting hepatocellular carcinoma as above-described. In the method, the using the protein marker further includes extracting from a surgically sampled biological sample.

According to another aspect of this invention, there is provided a method of detecting hepatocellular carcinoma as above-described. In the method, the verification is performed based on measurement of any one of a serine residue, a threonine residue, and a tyrosine residue of the protein marker for its phosphorylation.

According to still another aspect of this invention, there is provided a method of detecting hepatocellular carcinoma as above-described. In the method, the protein marker is extracted from a surgically sampled biological sample.

According to yet another aspect of this invention, there is provided a method of detecting hepatocellular carcinoma as above-described. In the method, the using the protein marker further includes preparing the biological sample which includes any one kind of a biopsy sample, blood, plasma, serum, and urine.

According to yet another aspect of this invention, there is provided a method of detecting hepatocellular carcinoma as above-described. In the method, the measuring further includes using an antibody that recognizes a phosphorylated site of the tumor rejection antigen gp96.

According to a still further aspect of this invention, there is provided a method of detecting hepatocellular carcinoma, which includes measuring phosphorylation of tumor rejection antigen gp96 as the hepatocellular carcinoma protein marker according to claim 1 in a biological sample, wherein the measuring is performed by a method selected from the group consisting of an enzyme immunoassay, a fluorescence-labeled antibody method, a western blot method, a radioimmunoassay, an immunoprecipitation method, electrophoresis, liquid chromatography, and mass spectrometry.

According to still another aspect of this invention, there is provided a method of detecting hepatocellular carcinoma, in which the phosphorylation is measured with respect to any one of a serine residue, a threonine residue, and a tyrosine residue of the hepatocellular carcinoma protein marker.

According to a yet further aspect of this invention, there is provided a method of detecting hepatocellular carcinoma as above-described. In the method, the measuring includes: extracting a protein from a surgically sampled biological sample; subjecting the protein to a multicycle of electrophoresis with different dimensions; fixing and staining the protein on a solid carrier; and comparing an increase or decrease in the tumor rejection antigen gp96 in a protein spot.

According to another aspect of this invention, there is provided a method of detecting hepatocellular carcinoma as above-described. In the method, the measuring further including preparing the biological sample comprising any one kind of a biopsy sample, blood, plasma, serum, and urine.

According to still another aspect of this invention, there is provided a method of detecting hepatocellular carcinoma as above-described. In the method, the measuring includes judging a presence or absence of hepatocellular carcinoma based on a comparison of the results obtained from measuring phosphorylation of a digestion product of the tumor rejection antigen gp96 obtained from a surgically sampled biological sample in positive ion mode measurement and in negative ion mode measurement by using a mass spectrometer.

According to yet another aspect of this invention, there is provided a method of detecting hepatocellular carcinoma as above-described. In the method, the measuring further includes preparing the biological sample comprising any one kind of a biopsy sample, blood, plasma, serum, and urine.

According to a further aspect of this invention, there is provided a method of detecting hepatocellular carcinoma as above-described. In the method, the measuring phosphorylation of the hepatocellular carcinoma protein marker is performed with respect to any one of a serine residue, a threonine residue, and a tyrosine residue of the protein marker.

According to a still further aspect of this invention, there is provided a method of detecting hepatocellular carcinoma as above-described. In the method, the measuring includes: extracting a protein from a surgically sampled biological sample; subjecting the protein to a multicycle of electrophoresis with different dimensions; fixing and staining the protein on a solid carrier; and comparing an increase or decrease in the tumor rejection antigen gp96 in a protein spot.

According to another aspect of this invention, there is provided a method of detecting hepatocellular carcinoma as above-described. In the method, the measuring includes judging a presence or absence of hepatocellular carcinoma based on a comparison of the results obtained from measuring phosphorylation of a digestion product of the tumor rejection antigen gp96 obtained from a surgically sampled biological sample in positive ion mode measurement and in negative ion mode measurement by using a mass spectrometer.

Effect of the Invention

The measurement of phospholation the tumor rejection antigen gp96 formed of the amino acid represented by SEQ ID NO: 1 can distinct hepatocellular carcinoma.

BRIEF DESCRIPTION OF THE DRAWINGS

FIG. 2 is a view showing the whole amino acid sequence of tumor rejection antigen gp 96.

FIG. 3 includes charts each showing a MALDI-TOF/MS spectrum of a product obtained by digesting tumor rejection antigen gp96 with trypsin. (a) shows the results in positive ion mode measurement and (b) shows the results in negative ion mode measurement.

Figure 1:
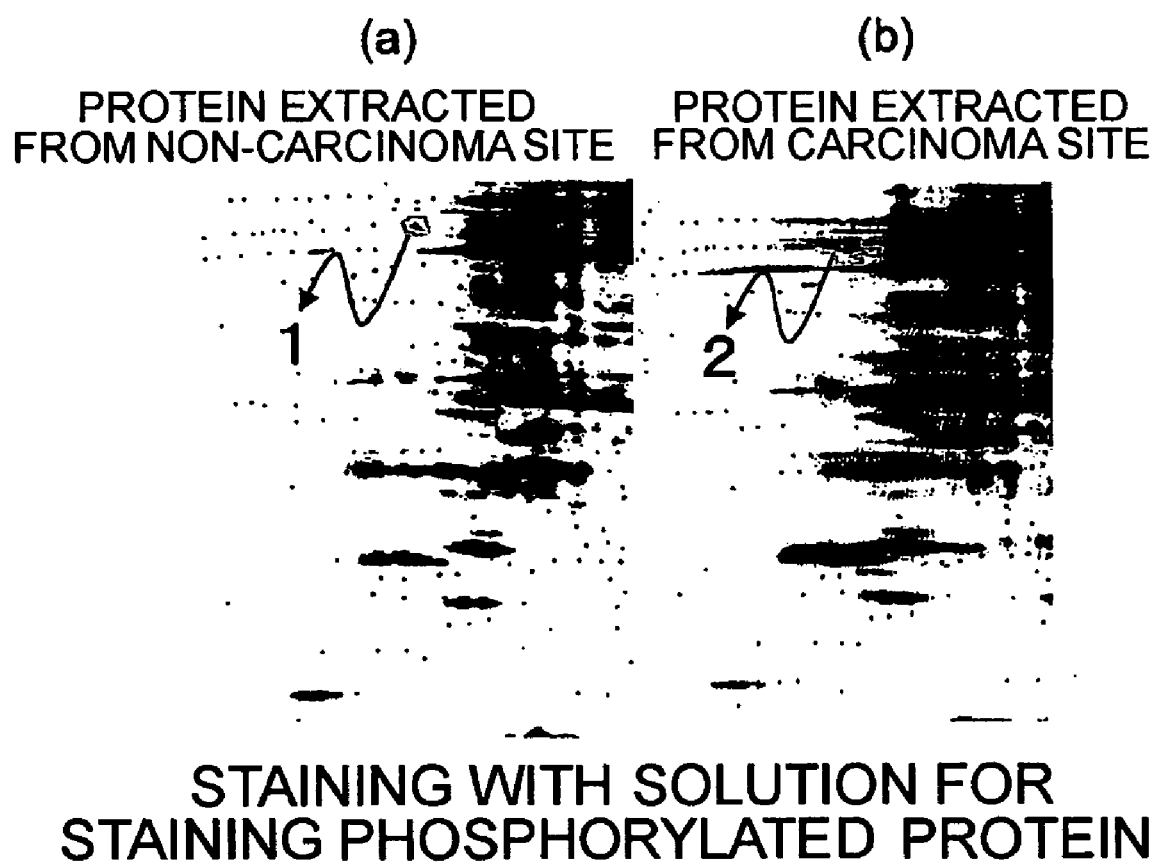
FIG. 1 shows a comparison between gels each stained with a solution for staining a phosphorylated protein after a protein sample extracted from a non-carcinoma site (a) and a protein sample extracted from a carcinoma site (b), which are obtained from 18 patients, have been developed by two-dimensional electrophoresis.

DESCRIPTION OF REFERENCE NUMBERS 1 spot of tumor rejection antigen gp96 of sample derived from non-carcinoma site
2 spot of tumor rejection antigen gp96 of sample derived from carcinoma site
41 peak derived from FQSSHHPTDITSLDQYVER peptide of tumor rejection antigen gp96 measured in positive ion mode
42 peak derived from FQSSHHPTDITSLDQYVER peptide of tumor rejection antigen gp96 measured in negative ion mode
43 peak derived from FQSSHHPTDITSLDQYVER peptide of phosphorylated tumor rejection antigen gp96 measured in negative ion mode

BEST MODE FOR CARRYING OUT THIS INVENTION

Hereinafter, this invention is described in more detail.

The inventors of this invention have researched a protein whose phosphorylation is accelerated in hepatocellular carcinoma tissues compared with non-carcinoma cells. As a result, the inventors have found that the phosphorylation amount of a specified protein may be measured to distinguish hepatocellular carcinoma cells from non-carcinoma cells. Thus, this invention has been completed.

That is, this invention relates to a method of assessing hepatocellular carcinoma by measuring the variation in phosphorylation of tumor rejection antigen gp96 formed of the amino acid represented by SEQ ID NO: 1 in a biological sample obtained from a subject.

Specifically, this invention provides a method of measuring tumor rejection antigen gp96 formed of the amino acid represented by SEQ ID NO: 1 for its phosphorylation by a method selected from the group consisting of an enzyme immunoassay, a fluorescence-labeled antibody method, a western blot method, a radioimmunoassay, an immunoprecipitation method, electrophoresis, liquid chromatography, and mass spectrometry.

In this case, the biological sample, such as a biopsy sample, blood, plasma, serum, and urine, can be used in this invention.

Examples of the method of measuring such variation in protein phosphorylation as described above in such a biological sample include: a method using in combination two-dimensional electrophoresis for separating a protein from the biological sample, which is a combination of isoelectric point electrophoresis and SDS polyacrylamide gel electrophoresis, and a staining method for allowing a phosphorylated state of the separated protein to be visualized; a method involving separating the biological sample by multidimensional chromatography, which is a combination of various types of chromatography such as ion-exchange chromatography, reverse-phase chromatography, and gel filtration chromatography, and determining the phosphorylation of the separated protein by mass spectrometry; and a method using a specified antibody that recognizes a phosphorylated site of a protein.

Further, the specified antibody according to this invention is an antibody which recognizes a phosphorylated serine residue, a phosphorylated threonine residue, and a phosphorylated tyrosine residue. The protein phosphorylation in a sample may be detected by using those antibodies alone or in combination, and employing a known method such as an enzyme immunoassay (ELISA), a western blotting method, a radioimmunoassay, and an immunoprecipitation method.

EXAMPLES

This invention is described in detail by way of examples, but this invention is not limited by those examples.

Example 1

In Example 1 of this invention, a two-dimensional electrophoresis analysis of proteins extracted from carcinoma cells and proteins extracted from non-carcinoma cells, which are derived from hepatocellular carcinoma patients, is described.

Carcinoma site tissues and non-carcinoma site tissues, which were obtained from tissues surgically excised from 18 hepatocellular carcinoma patients and were diagnosed pathologically, each were crushed in a cell lysis solution (30 mM Tris-Cl (pH 8.5), 7 M urea, 2 M thiourea, 4% (w/v) CHAPS, 0.5 mM EDTA, PMSF, Aprotinin, and Pepstatin) by using a glass homogenizer, followed by incubation at 37° C. for 1 hour. After the sample was centrifuged (13,000 rpm, 20 minutes), the supernatant was collected. The protein concentration in the supernatant was measured using a protein assay kit (manufactured by Bio-Rad Laboratories, Inc.) by a Bradford method. 25 μg of the protein extracted from a carcinoma site and 25 μg of the protein extracted from a non-carcinoma site, which had been sampled from each of the patients, were mixed to prepare a protein sample extracted from a carcinoma site (total: 450 μg) and a protein sample extracted from a non-carcinoma site (total: 450 μg). The protein samples extracted from a carcinoma site and the protein samples extracted from a non-carcinoma site were subjected to an isoelectric point electrophoresis at 71,500 Volt/hour by using an immobilized pH gradient gel (Immobiline DryStrip pH 3-10, 24 cm: GE Healthcare) (one-dimensional electrophoresis). The gel after being subjected to the one-dimensional electrophoresis was reduced-alkylated, a two-dimensional SDS electrophoresis was performed by using a 12.5% polyacrylamide gel (24 cm×20 cm). The gel subjected to the above-mentioned separation was stained with a solution for staining a phosphorylated protein (Pro-Q Diamond phosphoprotein gel stain: Invitrogen Corporation). The stained gel was detected for its protein spots with an image analyzer (Typhoon 9400: GE Healthcare UK Ltd).

A protein spot at which the staining with the solution for staining a phosphorylated protein varied more greatly in the carcinoma site compared with the non-carcinoma site was specified. The specified protein spot was cut out from the gel, and converted into a peptide by in-gel tryptic digestion. The in-gel digested peptide was measured with an ion spray mass spectrometer (ESI-MS, LCQ-Deca: Thermoelectron Corporation), and the protein at the spot was identified by a peptide mass fingerprint method (PMF method) using a Mascot software (MATRIX SCIENCE Ltd.).

The results revealed that the staining of the protein spot of the tumor rejection antigen gp96 with the solution for staining a phosphorylated protein varied more greatly in the carcinoma site compared with the non-carcinoma site.

FIG. 1 shows a comparison between gels each stained with the solution for staining a phosphorylated protein after the protein sample extracted from a carcinoma site and the protein sample extracted from a non-carcinoma site has been developed by two-dimensional electrophoresis. The reference numeral 1 in FIG. 1 denotes a spot of the tumor rejection antigen gp96 of a sample derived from the non-carcinoma site, and the reference numeral 2 denotes a spot of the tumor rejection antigen gp96 of a sample derived from the carcinoma site. With regard to the respective spots denoted as the reference numerals 1 and 2, the sample derived from the non-carcinoma site (1) and the sample derived from the carcinoma site (2) differ from each other in the staining with the solution for staining a phosphorylated protein. The spot denoted as the reference numeral 2 in FIG. 1 was cut out and subjected to in-gel tryptic digestion. After that, the protein was identified by the PMF method. As a result, as underlined in FIG. 2, a peptide having mass that corresponds to a partial peptide of the tumor rejection antigen gp96 was observed as a peptide obtained by subjecting the protein spot gel to tryptic digestion.

Example 2

In Example 2 of this invention, there is described the verification of the tumor rejection antigen gp96 for its phosphorylation by MALDI-TOF/MS measurement.

A product obtained by digesting the tumor rejection antigen gp96 with trypsin was dissolved in 10 μl of an aqueous solution containing 0.1% TFA and 50% methanol to obtain a sample solution. 1 μl of the sample solution was dropped onto a target plate for a mass spectrometer, and dried at room temperature. To the dried sample spot, dropped were 0.7 μl of a matrix solution (a solution obtained by dissolving α-cyano-4-hydroxycinnamic acid (α-CHCA) in a solution containing 0.1% trifluoroacetic acid (TFA), 70% methanol, and 4 mM mono ammonium phosphate so that the concentration would be a saturated concentration), followed by drying at room temperature. The target plate was measured with a time-of-flight mass spectrometer (MALDI-TOF/MS, Voyager DE STR: Applied Biosystems, Inc.) in a linear mode, and the ion polarity to be measured was measured in two ways, i.e., a positive ion mode and a negative ion mode. The mass in the spectrum was calibrated by an external standard method using a standard peptide.

FIG. 3 includes charts showing a comparison between the results in positive ion mode measurement and the results in negative ion mode measurement in a mass range of 699 Da to 3,001 Da. The negative ion mode can measure a mass spectrum of a phosphorylated peptide difficult to be measured in the positive ion mode.

Figure 4:
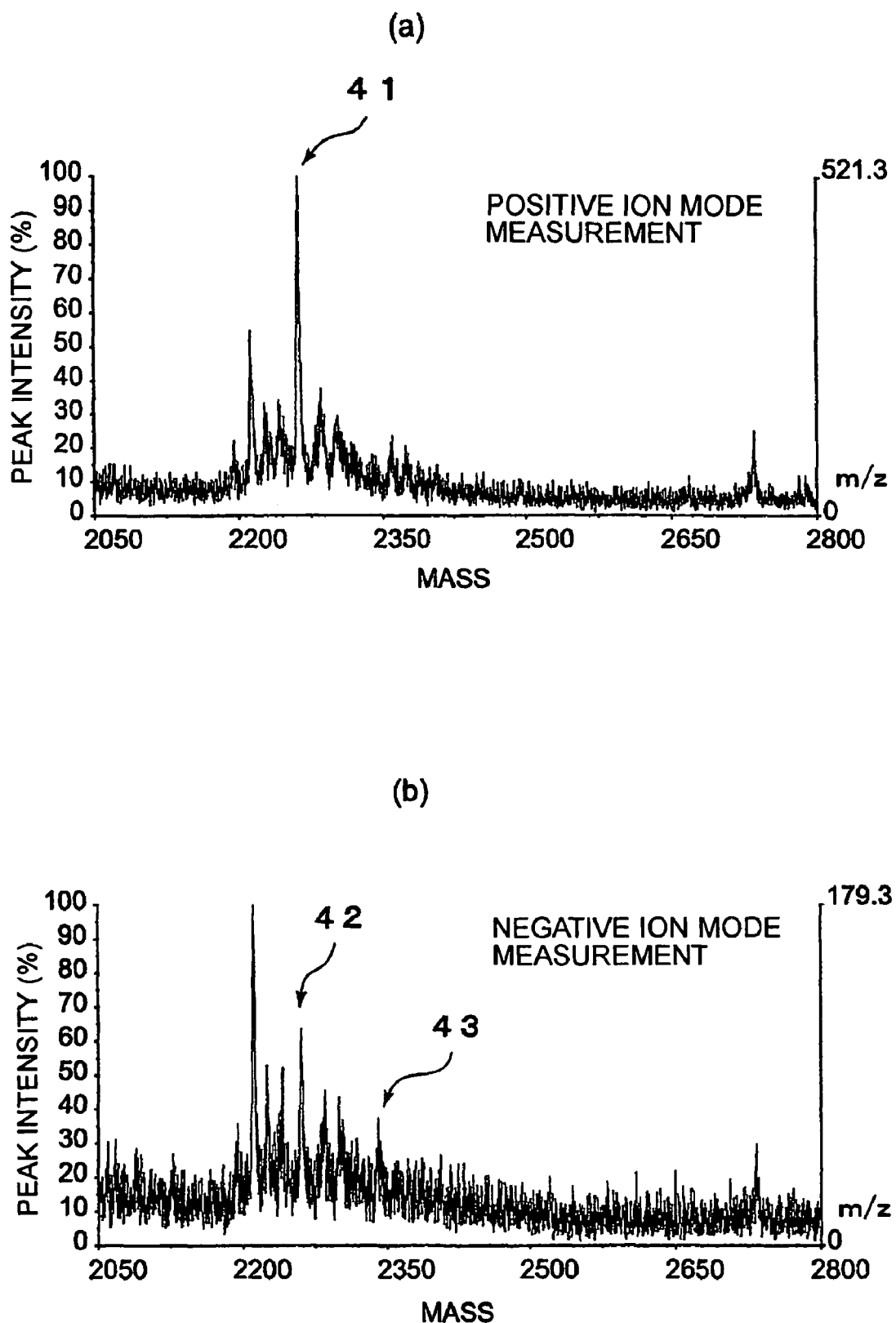
FIG. 4 includes charts each showing a MALDI-TOF/MS spectrum of a product obtained by digesting tumor rejection antigen gp96 with trypsin, and showing a comparison between the results in positive ion mode measurement (a) and the results in negative ion mode measurement (b) in a mass range of 2,050 Da to 2,800 Da.

FIG. 4 includes charts showing a comparison between mass spectra in a mass range of 2,050 Da to 2,800 Da. In FIG. 4, the reference numeral 41 denotes a peak derived from the FQSSHHPTDITSLDQYVER peptide of the tumor rejection antigen gp96 measured in the positive ion mode. Further, the reference numeral 42 denotes a peak derived from the FQSSHHPTDITSLDQYVER peptide of the tumor rejection antigen gp96 measured in the negative ion mode. Still further, 43 denotes a peak derived from the FQSSHHPT-DITSLDQYVER peptide of the phosphorylated tumor rejection antigen gp96 measured in the negative ion mode. As clear from FIG. 4, there is a peak observed only in the negative ion mode measurement (43 in FIG. 4) by a mass difference of +80 Da from a peak commonly observed in both of the positive ion mode measurement and the negative ion mode measurement (41 in FIG. 4 and 42 in FIG. 4). The mass of the peak commonly observed in both of the positive ion mode measurement and the negative ion mode measurement (41 in FIG. 4 and 42 in FIG. 4) coincides with the mass of the peptide of 512th to 530th residues (FQSSHHPTDITSLDQYVER) in the tumor rejection antigen gp96, and it is conceivable that any one of a serine residue (S), a threonine residue (T), and a tyrosine residue (Y) in FQSSHHPTDITSLDQYVER has been subjected to phosphorylation.

Accordingly, the measurement of the tumor rejection antigen gp96 for its phosphorylation is useful for diagnosis of hepatocellular carcinoma.

Industrial Applicability

This invention can provide the hepatocellular carcinoma protein marker and the method of detecting hepatocellular carcinoma cells using the hepatocellular carcinoma protein marker.

Note that the application of this invention insists advantage thereof based on the priority of Japanese Patent Application No. 2007-162857 filed on 20 Jun. 2007, and the disclosure of the filed application is taken into the whole of this application.

The invention claimed is:

1. An isolated protein comprising the amino acid sequence represented by SEQ ID NO: 1.

2. An isolated hepatocellular carcinoma protein marker, comprising: tumor rejection antigen gp96, wherein the protein marker is phosphorylated, and wherein said tumor rejection antigen gp96 comprises the amino acid sequence represented by SEQ ID NO: 1.

* * * * *

SEQUENCE LISTING

```
<160> NUMBER OF SEQ ID NOS: 1

<210> SEQ ID NO 1
<211> LENGTH: 803
<212> TYPE: PRT
<213> ORGANISM: homo sapiens

<400> SEQUENCE: 1

Met Arg Ala Leu Trp Val Leu Gly Leu Cys Cys Val Leu Leu Thr
                 5                  10                  15

Phe Gly Ser Val Arg Ala Asp Asp Glu Val Asp Val Asp Gly Thr
                20                  25                  30

Val Glu Glu Asp Leu Gly Lys Ser Arg Glu Gly Ser Arg Thr Asp
                35                  40                  45

Asp Glu Val Val Gln Arg Glu Glu Glu Ala Ile Gln Leu Asp Gly
                50                  55                  60

Leu Asn Ala Ser Gln Ile Arg Glu Leu Arg Glu Lys Ser Glu Lys
                65                  70                  75

Phe Ala Phe Gln Ala Glu Val Asn Arg Met Met Lys Leu Ile Ile
                80                  85                  90

Asn Ser Leu Tyr Lys Asn Lys Glu Ile Phe Leu Arg Glu Leu Ile
                95                 100                 105

Ser Asn Ala Ser Asp Ala Leu Asp Lys Ile Arg Leu Ile Ser Leu
               110                 115                 120

Thr Asp Glu Asn Ala Leu Ser Gly Asn Glu Glu Leu Thr Val Lys
               125                 130                 135

Ile Lys Cys Asp Lys Glu Lys Asn Leu Leu His Val Thr Asp Thr
               140                 145                 150

Gly Val Gly Met Thr Arg Glu Glu Leu Val Lys Asn Leu Gly Thr
               155                 160                 165

Ile Ala Lys Ser Gly Thr Ser Glu Phe Leu Asn Lys Met Thr Glu
               170                 175                 180

Ala Gln Glu Asp Gly Gln Ser Thr Ser Glu Leu Ile Gly Gln Phe
               185                 190                 195

Gly Val Gly Phe Tyr Ser Ala Phe Leu Val Ala Asp Lys Val Ile
               200                 205                 210

Val Thr Ser Lys His Asn Asn Asp Thr Gln His Ile Trp Glu Ser
               215                 220                 225

Asp Ser Asn Glu Phe Ser Val Ile Ala Asp Pro Arg Gly Asn Thr
               230                 235                 240

Leu Gly Arg Gly Thr Thr Ile Thr Leu Val Leu Lys Glu Glu Ala
               245                 250                 255
```

-continued

Ser Asp Tyr Leu Glu Leu Asp Thr Ile Lys Asn Leu Val Lys Lys
        260                 265                 270
Tyr Ser Gln Phe Ile Asn Phe Pro Ile Tyr Val Trp Ser Ser Lys
        275                 280                 285
Thr Glu Thr Val Glu Glu Pro Met Glu Glu Glu Ala Ala Lys
        290                 295                 300
Glu Glu Lys Glu Glu Ser Asp Asp Glu Ala Ala Val Glu Glu Glu
        305                 310                 315
Glu Glu Glu Lys Lys Pro Lys Thr Lys Val Glu Lys Thr Val
        320                 325                 330
Trp Asp Trp Glu Leu Met Asn Asp Ile Lys Pro Ile Trp Gln Arg
        335                 340                 345
Pro Ser Lys Glu Val Glu Glu Asp Glu Tyr Lys Ala Phe Tyr Lys
        350                 355                 360
Ser Phe Ser Lys Glu Ser Asp Asp Pro Met Ala Tyr Ile His Phe
        365                 370                 375
Tyr Ala Glu Gly Glu Val Thr Phe Lys Ser Ile Leu Phe Val Pro
        380                 385                 390
Thr Ser Ala Pro Arg Gly Leu Phe Asp Glu Tyr Gly Ser Lys Lys
        395                 400                 405
Ser Asp Tyr Ile Lys Leu Tyr Val Arg Arg Val Phe Ile Thr Asp
        410                 415                 420
Asp Phe His Asp Met Met Pro Lys Tyr Leu Asn Phe Val Lys Gly
        425                 430                 435
Val Val Asp Ser Asp Asp Leu Pro Leu Asn Val Ser Arg Glu Thr
        440                 445                 450
Leu Gln Gln His Lys Leu Leu Lys Val Ile Arg Lys Lys Leu Val
        455                 460                 465
Arg Lys Thr Leu Asp Met Ile Lys Lys Ile Ala Asp Asp Lys Tyr
        470                 475                 480
Asn Asp Thr Phe Trp Lys Glu Phe Gly Thr Asn Ile Lys Leu Gly
        485                 490                 495
Val Ile Glu Asp His Ser Asn Arg Thr Arg Leu Ala Lys Leu Leu
        500                 505                 510
Arg Phe Gln Ser Ser His His Pro Thr Asp Ile Thr Ser Leu Asp
        515                 520                 525
Gln Tyr Val Glu Arg Met Lys Glu Lys Gln Asp Lys Ile Thr Phe
        530                 535                 540
Met Ala Gly Ser Ser Arg Lys Glu Ala Glu Ser Ser Pro Phe Val
        545                 550                 555
Glu Arg Leu Leu Lys Lys Gly Tyr Glu Val Ile Tyr Leu Thr Glu
        560                 565                 570
Pro Val Asp Glu Tyr Cys Ile Gln Ala Leu Pro Glu Phe Asp Gly
        575                 580                 585
Lys Arg Phe Gln Asn Val Ala Lys Glu Gly Val Lys Phe Asp Glu
        590                 595                 600
Ser Glu Lys Thr Lys Glu Ser Arg Glu Ala Val Glu Lys Glu Phe
        605                 610                 615
Glu Pro Leu Leu Asn Trp Met Lys Asp Lys Ala Leu Lys Asp Lys
        620                 625                 630
Ile Glu Lys Ala Val Val Ser Gln Arg Leu Thr Glu Ser Pro Cys
        635                 640                 645
Ala Leu Val Ala Ser Gln Tyr Gly Trp Ser Gly Asn Met Glu Arg

-continued

```
                       650                 655                 660
Ile Met Lys Ala Gln Ala Tyr Gln Thr Gly Lys Asp Ile Ser Thr
                   665                 670                 675
Asn Tyr Tyr Ala Ser Gln Lys Lys Thr Phe Glu Ile Asn Pro Arg
                   680                 685                 690
His Pro Leu Ile Arg Asp Met Leu Arg Arg Ile Lys Glu Asp Glu
                   695                 700                 705
Asp Asp Lys Thr Val Leu Asp Leu Ala Val Val Leu Phe Glu Thr
                   710                 715                 720
Ala Thr Leu Arg Ser Gly Tyr Leu Leu Pro Asp Thr Lys Ala Tyr
                   725                 730                 735
Gly Asp Arg Ile Glu Arg Met Leu Arg Leu Ser Leu Asn Ile Asp
                   740                 745                 750
Pro Asp Ala Lys Val Glu Glu Glu Pro Glu Glu Glu Pro Glu Glu
                   755                 760                 765
Thr Ala Glu Asp Thr Thr Glu Asp Thr Glu Gln Asp Glu Asp Glu
                   770                 775                 780
Glu Met Asp Val Gly Thr Asp Glu Glu Glu Thr Ala Lys Glu
                   785                 790                 795
Ser Thr Ala Glu Lys Asp Glu Leu
                   800
```